United States Patent
Stein et al.

(10) Patent No.: US 11,596,368 B2
(45) Date of Patent: Mar. 7, 2023

(54) BREAST COMPRESSION PADDLES UTILIZING PIVOTING FOAM ELEMENTS

(71) Applicant: HOLOGIC, INC., Marlborough, MA (US)

(72) Inventors: Jay A. Stein, Marlborough, MA (US); Kenneth F. Defreitas, Marlborough, MA (US); Richard Gladwin Edwards, Marlborough, MA (US); Brad Michael Keller, Marlborough, MA (US); Christine Janssen, Marlborough, MA (US); Alan Rego, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 34 days.

(21) Appl. No.: 16/981,943

(22) PCT Filed: May 24, 2019

(86) PCT No.: PCT/US2019/034001
§ 371 (c)(1),
(2) Date: Sep. 17, 2020

(87) PCT Pub. No.: WO2019/227044
PCT Pub. Date: Nov. 28, 2019

(65) Prior Publication Data
US 2021/0361246 A1    Nov. 25, 2021

Related U.S. Application Data

(60) Provisional application No. 62/814,041, filed on Mar. 5, 2019, provisional application No. 62/732,771, filed (Continued)

(51) Int. Cl.
*A61B 6/04* (2006.01)
*A61B 6/00* (2006.01)
(Continued)

(52) U.S. Cl.
CPC .......... *A61B 6/0414* (2013.01); *A61B 6/0435* (2013.01); *A61B 6/502* (2013.01); *A61B 6/025* (2013.01); *A61B 6/032* (2013.01)

(58) Field of Classification Search
CPC ....... A61B 6/025; A61B 6/032; A61B 6/0414; A61B 6/0435; A61B 6/502
See application file for complete search history.

(56) References Cited

U.S. PATENT DOCUMENTS 4,744,099 A    5/1988   Huettenrauch et al.
5,506,877 A *  4/1996   Niklason ................ A61B 6/502
                                                          378/208
(Continued)

FOREIGN PATENT DOCUMENTS

JP    2011-206436 A    10/2011
JP    2011206436 A  *  10/2011

OTHER PUBLICATIONS

English translation of JP2011206436 (Year: 2011).*
(Continued)

*Primary Examiner* — Dani Fox
*Assistant Examiner* — Soorena Kefayati
(74) *Attorney, Agent, or Firm* — Merchant & Gould P.C.

(57) ABSTRACT

A breast compression paddle has two sidewalls, each having an upper edge. Spanning the two side walls is a leading wall which also has an upper edge and is disposed distal from a bracket that is connected to a compression arm. Foam is secured to a substrate which is movably secured to the bracket and the rigid frame between a first position and a second position. In the first position, portions of the substrate and foam are disposed above the upper edges of all three walls. In the second position, the substrate and all of the foam is disposed below the upper edges of all three walls.

7 Claims, 10 Drawing Sheets

Related U.S. Application Data on Sep. 18, 2018, provisional application No. 62/676,609, filed on May 25, 2018.

(51) Int. Cl.
  *A61B 6/02* (2006.01)
  *A61B 6/03* (2006.01)

(56) References Cited

U.S. PATENT DOCUMENTS

| | | | | |
|---|---|---|---|---|
| 6,577,702 | B1* | 6/2003 | Lebovic | A61B 6/502 378/68 |
| 8,401,145 | B1* | 3/2013 | Boutte | A61B 6/502 378/208 |
| 9,883,846 | B2* | 2/2018 | Son | A61B 6/0421 |
| 2003/0007597 | A1* | 1/2003 | Higgins | A61B 6/0414 378/37 |
| 2004/0218727 | A1* | 11/2004 | Shoenfeld | A61B 6/0414 378/167 |
| 2005/0008117 | A1* | 1/2005 | Livingston | A61B 6/0414 378/37 |
| 2006/0050844 | A1* | 3/2006 | Galkin | A61B 6/4283 378/37 |
| 2006/0126794 | A1* | 6/2006 | Hermann | A61B 6/0414 378/180 |
| 2007/0280412 | A1* | 12/2007 | Defreitas | A61B 6/0414 378/37 |
| 2010/0067659 | A1* | 3/2010 | Bush | A61N 5/1049 378/68 |
| 2010/0179604 | A1* | 7/2010 | Campagna | A61B 6/0421 606/86 A |
| 2012/0114096 | A1* | 5/2012 | Lebovic | A61B 6/0435 378/208 |
| 2013/0129039 | A1* | 5/2013 | DeFreitas | A61B 6/0414 378/208 |
| 2014/0177791 | A1 | 6/2014 | Otokuni et al. | |
| 2015/0250432 | A1* | 9/2015 | Savagian | A61B 6/0407 378/208 |
| 2015/0305693 | A1* | 10/2015 | Galambos McLaughlin | A61B 6/502 5/601 |
| 2016/0081633 | A1* | 3/2016 | Stango | A61B 6/04 378/37 |
| 2016/0183898 | A1 | 6/2016 | Cormican | |
| 2016/0206229 | A1 | 7/2016 | Arai et al. | |
| 2017/0340303 | A1* | 11/2017 | Stango | A61B 90/17 |
| 2021/0015435 | A1 | 1/2021 | DeFreitas | |
| 2021/0030375 | A1 | 2/2021 | Defreitas et al. | |

OTHER PUBLICATIONS

Machine translation of JP-2011206436. (Year: 2011).*
International Search Report and Written Opinion of the International Searching Authority for International Patent Application No. PCT/US2019/034001 dated Jul. 31, 2019, 12 pages.
PCT International Preliminary Report on Patentability in International Patent Application No. PCT/US2019/034001, dated Dec. 10, 2020, 8 pages.

* cited by examiner

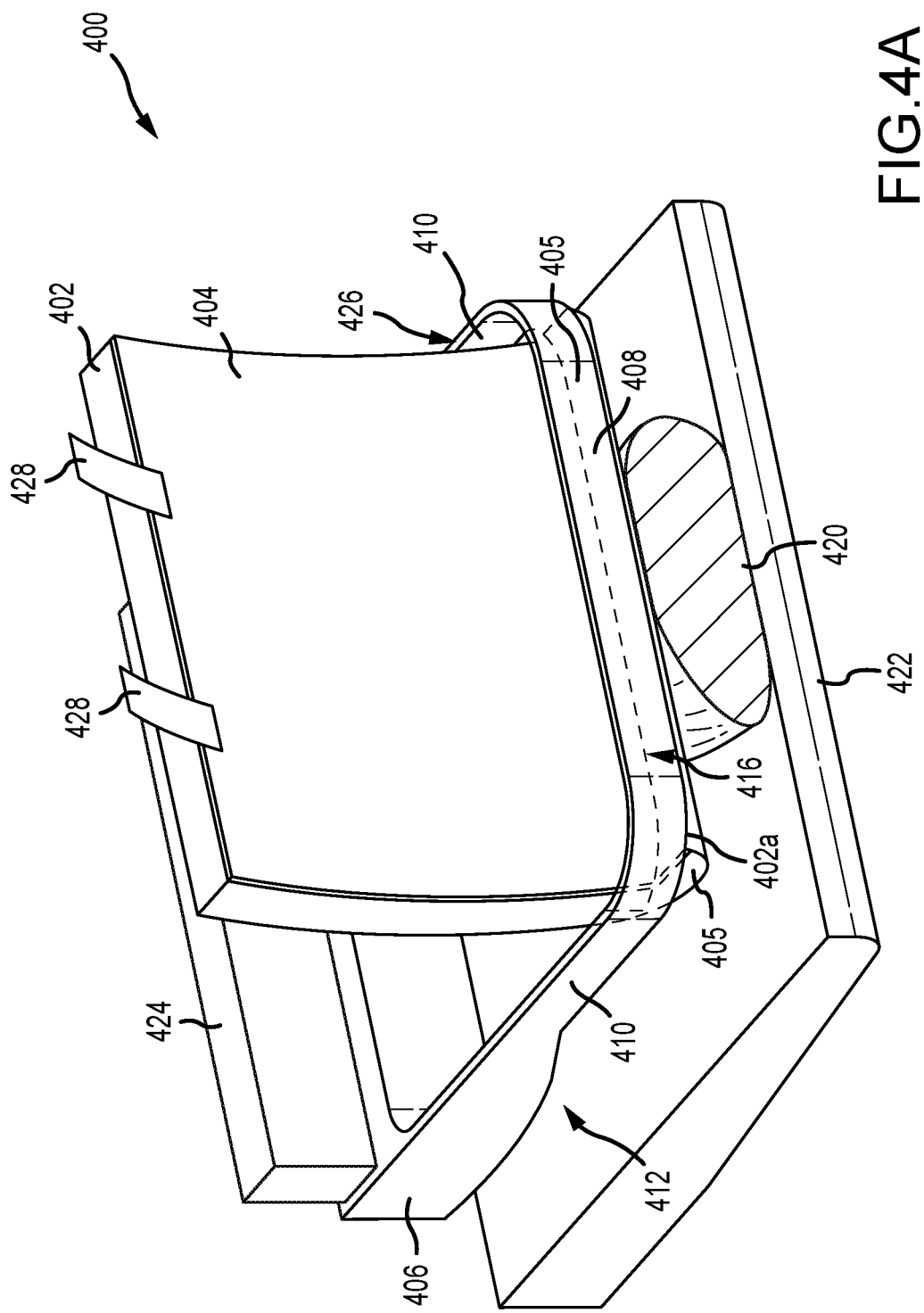

BREAST COMPRESSION PADDLES UTILIZING PIVOTING FOAM ELEMENTS

CROSS-REFERENCE TO RELATED APPLICATIONS

This application is a National Stage Application of PCT/US2019/034001, filed on May 24, 2019, which claims the benefit of priority to U.S. Provisional Application No. 62/676,609, filed May 25, 2018, U.S. Provisional Application No. 62/732,771, filed Sep. 18, 2018, and U.S. Provisional Application No. 62/814,041, filed Mar. 5, 2019, which applications are hereby incorporated in their entireties by reference. To the extent appropriate, a claim of priority is made to each of the above disclosed applications.

BACKGROUND

Compression during mammography and tomosynthesis imaging serves a number of purposes. For example, it: (1) makes the breast thinner in the direction of x-ray flux and thereby reduces patient radiation exposure from the level required to image the thicker parts of a breast that are not compressed; (2) makes the breast more uniform in thickness in the direction of x-ray flux and thereby facilitates more uniform exposure at the image plane over the entire breast image; (3) immobilizes the breast during the x-ray exposure and thereby reduces image blurring; and (4) brings breast tissues out from the chest wall into the imaging exposure field and thus allows for more tissue imaging. As the breast is being compressed, typically a technologist manipulates the breast to position it appropriately and counter the tendency that compression has of pushing breast tissue toward the chest wall and out of the image field.

Standard compression methods for mammography and tomosynthesis use a movable, rigid, radiolucent compression paddle. The breast is placed on a breast support platform that typically is flat, and the paddle then compresses the breast, usually while a technologist or other health professional is holding the breast in place. The technologist may also manipulate the breast to ensure proper tissue coverage in the image receptor's field of view.

One known challenge in mammography and breast tomosynthesis is the discomfort the patient may feel when the breast is compressed, which must be done with sufficient force to immobilize the breast and spread out the breast tissues for x-ray imaging. Discomfort may potentially cause the patient to move, which negatively impacts image quality. Discomfort may also potentially dissuade patients from getting screened for breast cancer. Another known challenge is to ensure that the imaged field includes the desired amount of breast tissue.

SUMMARY

In one aspect, the technology relates to a breast compression paddle including: a bracket for removably securing the breast compression paddle to an imaging system; a rigid frame secured to the bracket, wherein the rigid frame includes: two side walls, each having a side wall upper edge, wherein each of the two side walls extends from the bracket; and a leading wall having a leading wall upper edge, wherein the leading wall is disposed distal from the bracket, wherein the leading wall spans the two side walls; a substrate movably secured to at least one of the bracket and the rigid frame between a first position and a second position, wherein when in the first position, at least a portion of the substrate is disposed above the upper edges of the two side walls and the upper edge of the leading wall, and wherein when in the second position, the substrate is disposed below the upper edges of the two side walls and the upper edge of the leading wall; and a foam secured to the substrate, and wherein when in the first position, at least a portion of the foam is disposed above the upper edges of the two side walls and the upper edge of the leading wall, and wherein when in the second position, an entire volume of the foam is disposed below the upper edges of the two side walls and the upper edge of the leading wall. In an example, the substrate is rigid. In another example, the substrate is movably secured to the bracket at an edge proximate the bracket. In yet another example, the breast compression paddle further includes a strut system, wherein the strut system movably secures the substrate to the bracket. In still another example, the edge has at least one of a live hinge and a pivoting hinge.

In another example of the above aspect, the substrate is pivotably connected to the frame proximate a mid-point of the frame and the substrate. In an example, the frame is pivotably connected to the bracket. In another example, the bracket has an element configured to be slidably connected to a compression arm of an imaging system. In yet another example, at least a portion of the leading wall is curved. In still another example, the substrate is flexible.

In another example of the above aspect, the leading wall includes a vertical portion and a substantially horizontal portion. In an example, the foam is further secured to the substantially horizontal portion. In another example, the foam movably connects the substrate to the frame.

BRIEF DESCRIPTION OF THE DRAWINGS

FIGS. 4A-4C depict another example of a compression paddle having a movable foam compressive element, at various positions during compression procedures.

DETAILED DESCRIPTION

Figure 1A:
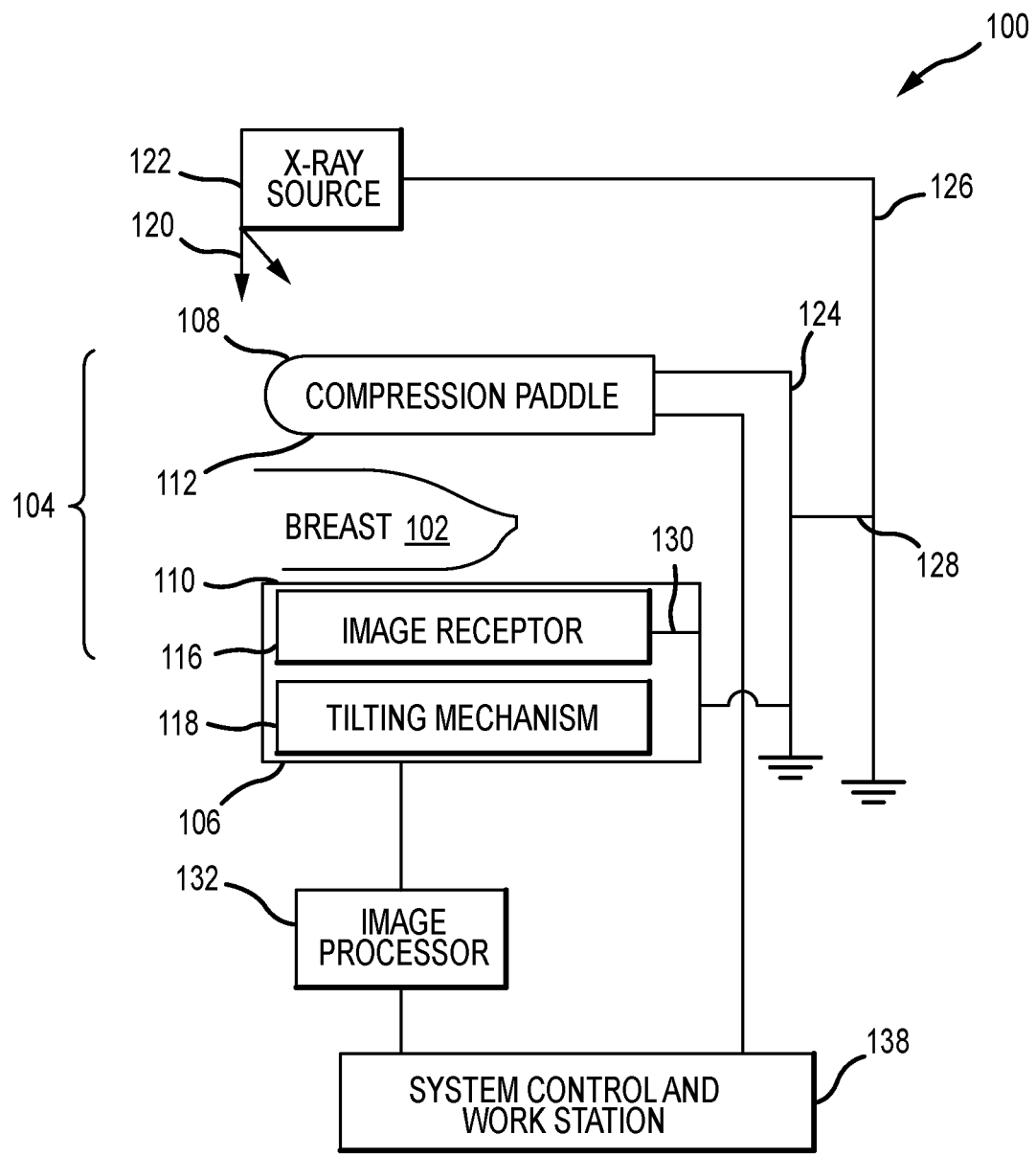
FIG. 1A is a schematic view of an exemplary imaging system.
Figure 1B:
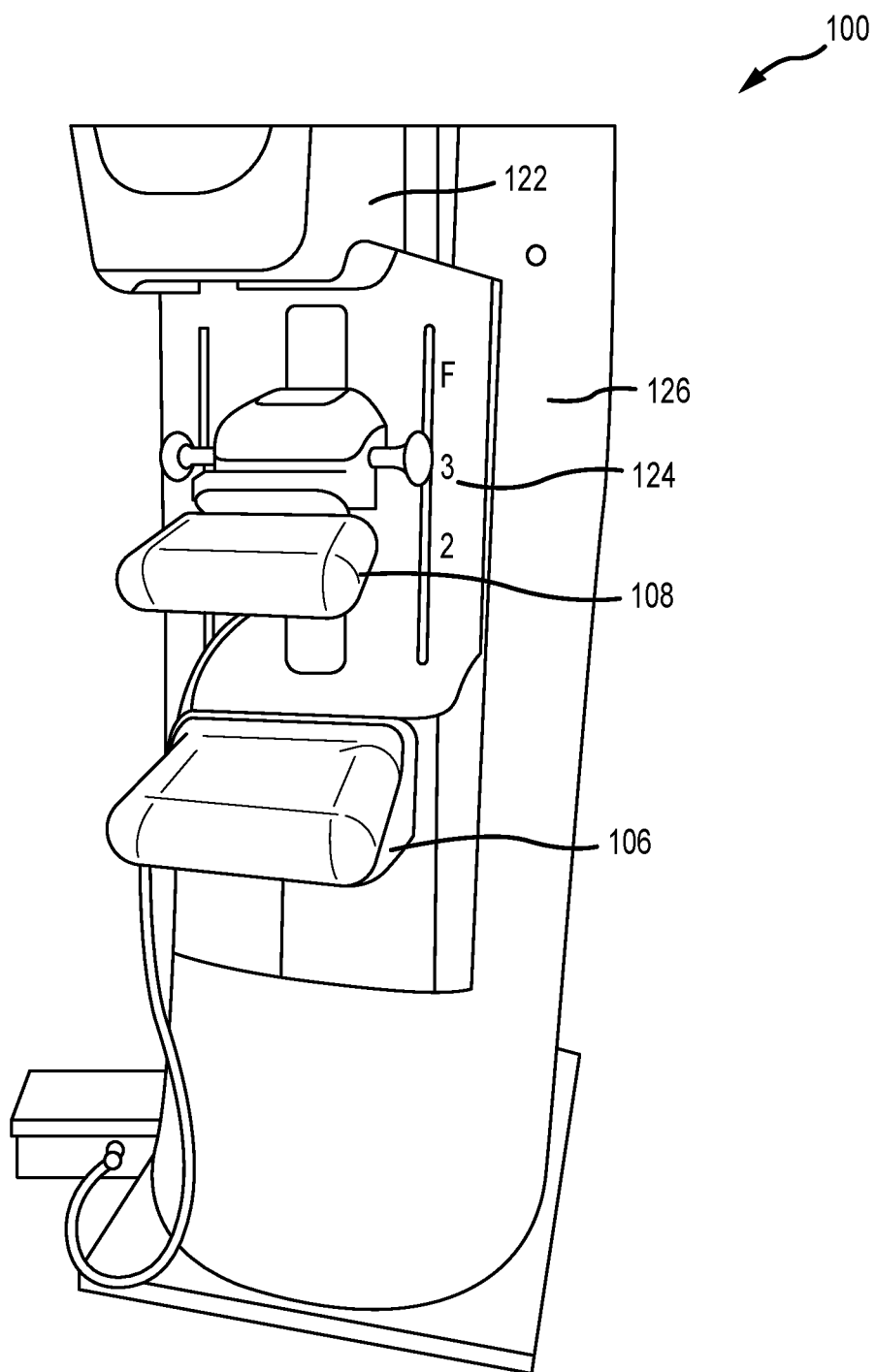
FIG. 1B is a perspective view of the imaging system of FIG. 1A.

FIG. 1A is a schematic view of an exemplary imaging system 100. FIG. 1B is a perspective view of the imaging system 100. Referring concurrently to FIGS. 1A and 1B, the imaging system 100 immobilizes a patient's breast 102 for x-ray imaging (either or both of mammography and tomosynthesis) via a breast compression immobilizer unit 104 that includes a static breast support platform 106 and a moveable compression paddle 108. The breast support platform 106 and the compression paddle 108 each have a compression surface 110 and 112, respectively, that move towards each other to compress and immobilize the breast 102. In known systems, the compression surface 110, 112 is exposed so as to directly contact the breast 102. The platform 106 also houses an image receptor 116 and, optionally, a tilting mechanism 118, and optionally an anti-scatter grid. The immobilizer unit 104 is in a path of an imaging beam 120 emanating from x-ray source 122, such that the beam 120 impinges on the image receptor 116.

The immobilizer unit 104 is supported on a first support arm 124 and the x-ray source 122 is supported on a second support arm 126. For mammography, support arms 124 and 126 can rotate as a unit about an axis 128 between different imaging orientations such as CC and MLO, so that the system 100 can take a mammogram projection image at each orientation. In operation, the image receptor 116 remains in place relative to the platform 106 while an image is taken. The immobilizer unit 104 releases the breast 102 for movement of arms 124, 126 to a different imaging orientation. For tomosynthesis, the support arm 124 stays in place, with the breast 102 immobilized and remaining in place, while at least the second support arm 126 rotates the x-ray source 122 relative to the immobilizer unit 104 and the compressed breast 102 about the axis 128. The system 100 takes plural tomosynthesis projection images of the breast 102 at respective angles of the beam 120 relative to the breast 102.

The image receptor 116 may be tilted relative to the breast support platform 106 and in sync with the rotation of the second support arm 126. The tilting can be through the same angle as the rotation of the x-ray source 122, but may also be through a different angle selected such that the beam 120 remains substantially in the same position on the image receptor 116 for each of the plural images. The tilting can be about an axis 130, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The system 100 can be solely a mammography system, a CT system, or solely a tomosynthesis system, or a "combo" system that can perform multiple forms of imaging. An example of such a combo system has been offered by the assignee hereof under the trade name Selenia Dimensions.

When the system is operated, the image receptor 116 produces imaging information in response to illumination by the imaging beam 120, and supplies it to an image processor 132 for processing and generating breast x-ray images. A system control and work station unit 138 including software controls the operation of the system and interacts with the operator to receive commands and deliver information including processed-ray images.

One challenge with the imaging system 100 is how to immobilize and compress the breast 102 for the desired or required imaging. A health professional, typically an x-ray technologist, generally adjusts the breast 102 within the immobilizer unit 104 while pulling tissue towards imaging area and moving the compression paddle 108 toward the breast support platform 106 to immobilize the breast 102 and keep it in place, with as much of the breast tissue as practicable being between the compression surfaces 110, 112.

The present technology relates to a breast compression system having a foam compressive element and/or other components as described below for use in a breast imaging system. During imaging of a breast, it is often desirable to immobilize the breast through compression. For instance, by compressing the breast, the breast can be made thinner, thus requiring a lower dose of radiation. Further, by immobilizing the breast, image blurring from movement of the breast during imaging is reduced. Other benefits may also be realized by compressing the breast.

The paddle may also cause discomfort to the patient whose breast is being compressed. One reason for discomfort that the patient may feel is that the compression force is non-uniformly distributed throughout the breast. It is often concentrated at the thickest portion of the breast, usually near the chest wall, at or near the lower front edge of the compression paddle and the upper front corner of the breast platform. The anterior portion of the breast, such as near the nipple, may receive less compressive force, or no compressive force. The paddle may not even contact this portion of the breast. (The terms front, lower, and upper pertain to using a craniocaudal (CC) imaging orientation, with the patient facing the front of the imaging system, although it should be understood that other imaging orientations, including mediolateral oblique (MLO), are used with the same equipment.)

To improve these issues, the compression systems described herein include a foam compressive element that is positioned over a compression surface and contacts the breast during compression. Although described generally in the context of foam disposed on a compression paddle, foam may additionally or alternatively be disposed on a breast support platform. The foam compresses as pressure increases and is generally more comfortable than hard plastic paddles. Other features may be utilized to improve technologist visibility of the breast during compressive procedures, as well as to determine the amount of foam compression. Appropriate foam materials include super soft urethane foams, such as fire-retardant upholstery foams, that display advantageous performance characteristics. Such materials may be manufactured so as to meet the requirements of ASTM D 3574. Foams having the performance characteristics displayed in Table 1 below have displayed advantageous properties, although other foams having different performance characteristics may also be utilized.

TABLE 1

| Super Soft Foam Performance Data | | |
|---|---|---|
| Property | Test Method | Values |
| Density (LB/Cubic Ft.) | ASTM D 3574 | 1.2 |
| 25% ILD (LB) | ASTM D 3574 | 12 |
| Support Factor (65%/25% Min.) | ASTM D 3574 | 1.9 |
| Air Flow (CFM) Min. | ASTM D 3574 | 3 |
| Tensile (PSI) Min. | ASTM D 3574 | 10 |
| Elongation (%) Min. | ASTM D 3574 | 200 |
| Tear (PPI) Min. | ASTM D 3574 | 1.1 |
| Resiliency (%) Min. | ASTM D 3574 | 40 |

Further testing has been performed to identify desirable foams that may be utilized as thick foam compressive elements. For example, a noise power spectrum study has been performed. In the study, a 2 inch piece of foam was compressed to various thicknesses on a Selenia Dimensions system available from the assignee hereof. Detector signals were all matched in the study and it was determined that noise changes were all due to the utilization of a foam compressive element. It was further determined that compression helps to reduce the noise generated by the foam, expect when compressed to below 2 cm thickness where further noise reduction becomes less significant. As the magnitude was increased, a spectrum shape change was also observed. Further, the noise from the foam was both high and low frequency, although low frequency noise was more enhanced in the foam images. Further results are depicted in Tables 2 and 3, below.

TABLE 2

Magnitude Study

| | sig | nos | nos ratio |
|---|---|---|---|
| no foam | 471 | 6.31 | 1.000 |
| foam at 0 cm | 469 | 7.11 | 1.127 |
| foam at 10 cm | 470 | 6.88 | 1.090 |
| foam at 20 cm | 471 | 6.70 | 1.062 |
| foam at 34 cm | 472 | 6.54 | 1.036 |

TABLE 3

Compression Study

| | sig | nos | nos ratio |
|---|---|---|---|
| no foam | 471 | 6.31 | 1.000 |
| foam of 5.2 cm | 472 | 7.09 | 1.123 |
| foam of 2 cm | 472 | 6.86 | 1.087 |
| foam of 1 cm | 472 | 6.81 | 1.080 |
| foam of 0.6 cm | 472 | 6.79 | 1.076 |

The foam may be secured to a hard plastic compression paddle substrate with a radiotranslucent adhesive, or may be mechanically secured thereto, for example, with hooks, straps, or other securement structures. The foam at least partially conforms in shape to the breast as the paddle is lowered and the foam compresses. This stabilizes and may entirely immobilize (or a portion thereof) the breast for imaging, without requiring the compression pressure typical in breast imaging systems. Additionally, the foam may be placed on the portions of the compression paddle and breast platform that face the chest wall. As the compression paddle is lowered, the foam compresses and takes on a curved shaped that approximates the shape of the breast. However, unlike hard plastic compression paddles, compression forces need not be so high as to completely flatten the breast. Rather, the foams described herein are utilized to stabilize the breast, not necessarily to effectuate full compression, which is usually performed by flat rigid compression paddles (or by breast compression elements that have a very thin layer of foam disposed thereon. In a traditional mammogram system, since the breast is not flat, the appearance of the breast would differ (depending on the level of compression of the particular volume of interest), although this appearance may be corrected by image processing algorithms. For imaging systems such as tomosynthesis, however, the foam only appears in slices outside of the boundaries of the breast. For slices inside the breast, the structures blur out and are not visible. As such, the paddles utilizing foams described herein may be used for both mammography and tomosynthesis imaging, although some post-imaging processing may be required to realize all advantages thereof.

The proposed technology contemplates a number of features. For example, the foam may be rectangular in shape and have outer dimensions sized to match the image receptor size. For ease of manufacturing, the foam may be uniformly shaped, such as a rectangular prism. Other alternative examples may include a non-uniform shape, such as greater thickness at breast contacting portion or greater thickness at edges. Greater thickness at the areas of the foam proximate the edges of the breast may help the foam further conform to and stabilize the breast. In examples, the foam may include a width between lateral edge surfaces thereof, and a length between a leading edge surface and a trailing edge surface. In one example, the dimensions of the foam may be about 30 cm wide×24 cm long. In examples, the foam may be about 3 inches thick, about 2 inches thick, or about 1 inch thick. The desired thickness may be dependent on a number of factors including breast size, breast density, compression paddle size, and so on. As noted elsewhere herein, the foam may include a mounting mechanism for connection to a compression paddle or a breast platform. In examples, the mounting mechanism may instead be a permanent or semi-permanent adhesive.

A cover may be disposed on the surfaces of the foam that contact the breast. The cover prevents the foam from absorbing sweat or other bodily fluids which may cause damage to the foam or unsanitary conditions. The cover may be anti-microbial, cleanable, and fluid-resistant; it is also desirable that the cover is sufficiently pliable so as not to adversely affect the deformation of the foam during compression. The cover should also be resistant to cleaning chemicals that may be utilized to sanitize the cover between patients. Disposable covers are also contemplated. Such covers may be easier to use; technologists may simply remove and dispose of the cover between patients. By applying the cover prior to a new procedure, the technologist may give the patient a further impression of being in a sanitary facility. Disposable covers may be stored in a dispenser within the procedure room or on the imaging equipment. In another example, the cover may be formed of a continuous roll of appropriate material mounted on the compression paddle (e.g., proximate a bracket thereof), but removed from the imaging area. A new clean portion of cover may be unrolled and placed into contact with the foam for each new patient.

Compression paddles are typically manufactured from a clear rigid material that enables a technician operating a breast imaging system to view the breast at various points during breast positioning and imaging. This allows the technician to properly access the breast, for example, to avoid wrinkles in the tissue, to properly position the nipple, etc. The foam compressive technologies described herein, while allowing for greater comfort for the patient, can reduce access to and visibility of the breast by the technician. Thus, the foam compressive material described herein are advantageously used in conjunction with other technologies also described herein that improve access to the breast. Briefly, these technologies include those that enable visibility of and access to the breast as the compression paddle incorporating foam is lowered to compress the breast. In examples, structural features of the breast compression paddles described herein are used to first stabilize the breast while the breast remains visible to the technician, and prior to the point where significant compression is undertaken. Other technologies contemplate moving of the breast compression paddle so as to reduce the amount of time that visibility of or access to the breast is reduced or limited. These and other relevant technologies are described in further detail below.

Figure 2A:
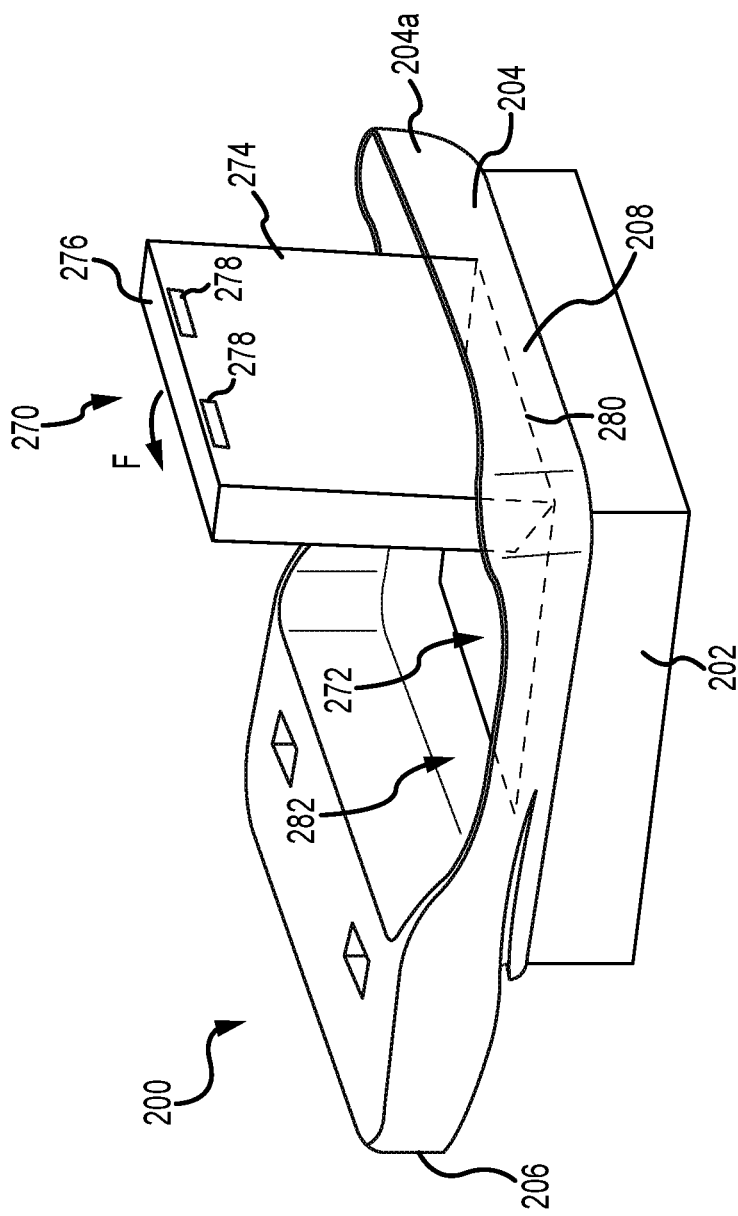
FIG. 2A is a perspective view of a compression paddle having a hinged portion of a foam compressive element in accordance with another example.

FIG. 2A is a top perspective view of a compression paddle 200 having a hinged portion 270 of a foam compressive element in accordance with another example. The paddle 200 includes a bracket portion 206, generally integral with the substrate 204 for connecting the paddle to compression arm of an imaging system. The paddle 200 also includes a leading face 208, opposite the bracket portion 206, which is disposed proximate a chest wall of a patient during compression and imaging procedures. A foam compressive material 202, such as described elsewhere herein, is secured to a bottom of the substrate 204. Raised walls 204a provide additional rigidity. The hinged portion 270 may be used to increase visibility of the breast to improve ease of positioning and AEC procedures. The breast (not shown) may be initially positioned with the hinged portion 270 open, thus forming a window 272 in the top of the compression paddle 200. Once initially compressed, the hinged portion 270 may be folded down F towards the breast. The hinged portion 270 includes a rigid portion 274 and a foam portion 276 secured thereto. The rigid portion 274 may be referred to as a subsidiary rigid portion 274 as compared to the main rigid substrate 204. Foam portion 276 may also be referred to as subsidiary portion 276. Slide bolts, hasps, or other locking features 278 may secure the hinged portion 270 to the substrate 204 of the compression paddle 200. Thereafter, compression may continue until the breast reaches the imaging condition. In another example, the hinged portion 270 may be secured once the breast has been compressed to the imaging condition. The rigid portion 274 of the hinged portion 270 may be formed of the same material as the remainder of the substrate 204 or may be formed of a material displaying greater or less rigidity. A hinge 280, which in examples is a living hinge, a mechanical hinge, or other pivotable connecting feature, may secure the rigid portion 274 to the substrate 204 proximate the leading edge surface 208. In examples where the rigid portion 274 is less rigid than the substrate 204, the rigid portion may be folded down below a top surface 282 of the substrate 204, for greater conformance with the breast. The compression paddle 200 depicted in FIG. 2A has at least one advantage in that the foam compressive material 202 proximate the leading edge surface may be first compressed against the breast so as to draw breast tissue away from the chest wall. Thereafter, the hinged portion 270 may be applied to the breast so as to prevent pushing of breast tissue back towards the chest wall. The foam compressive material 202, as well as the foam portion 276, may be configured as described elsewhere herein.

Figure 2B:
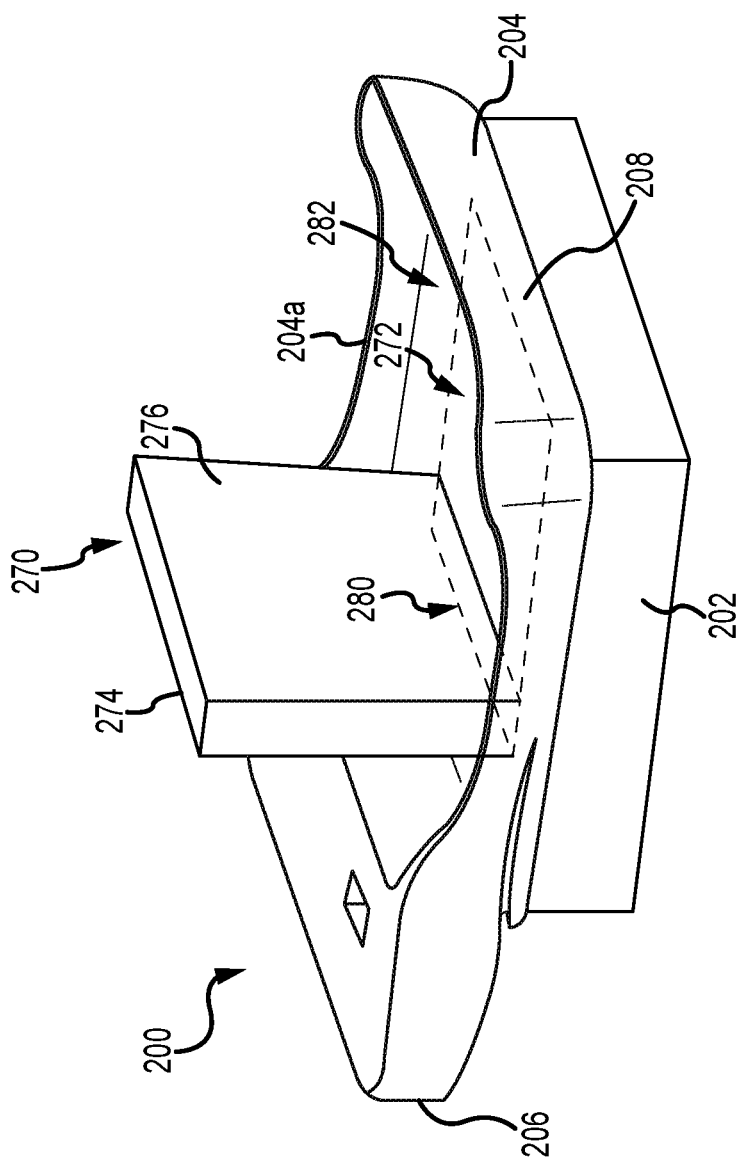
FIG. 2B is a perspective view of a compression paddle having a hinged portion of a foam compressive element in accordance with another example.

FIG. 2B is a top perspective view of a compression paddle 200 having a hinged portion 270 of a foam compressive element in accordance with another example. A number of elements are described above with regard to FIG. 2A and, as such, are not described further. Notably, a hinged portion 270 is connected with a hinge 280, which in examples is a living hinge, a mechanical hinge, or other pivotable connecting feature, to the substrate 204 proximate the bracket 206. The paddle 200 depicted in FIG. 2B is therefore similar in operation and advantage to the paddle 200 of FIG. 2A.

Figure 3A:
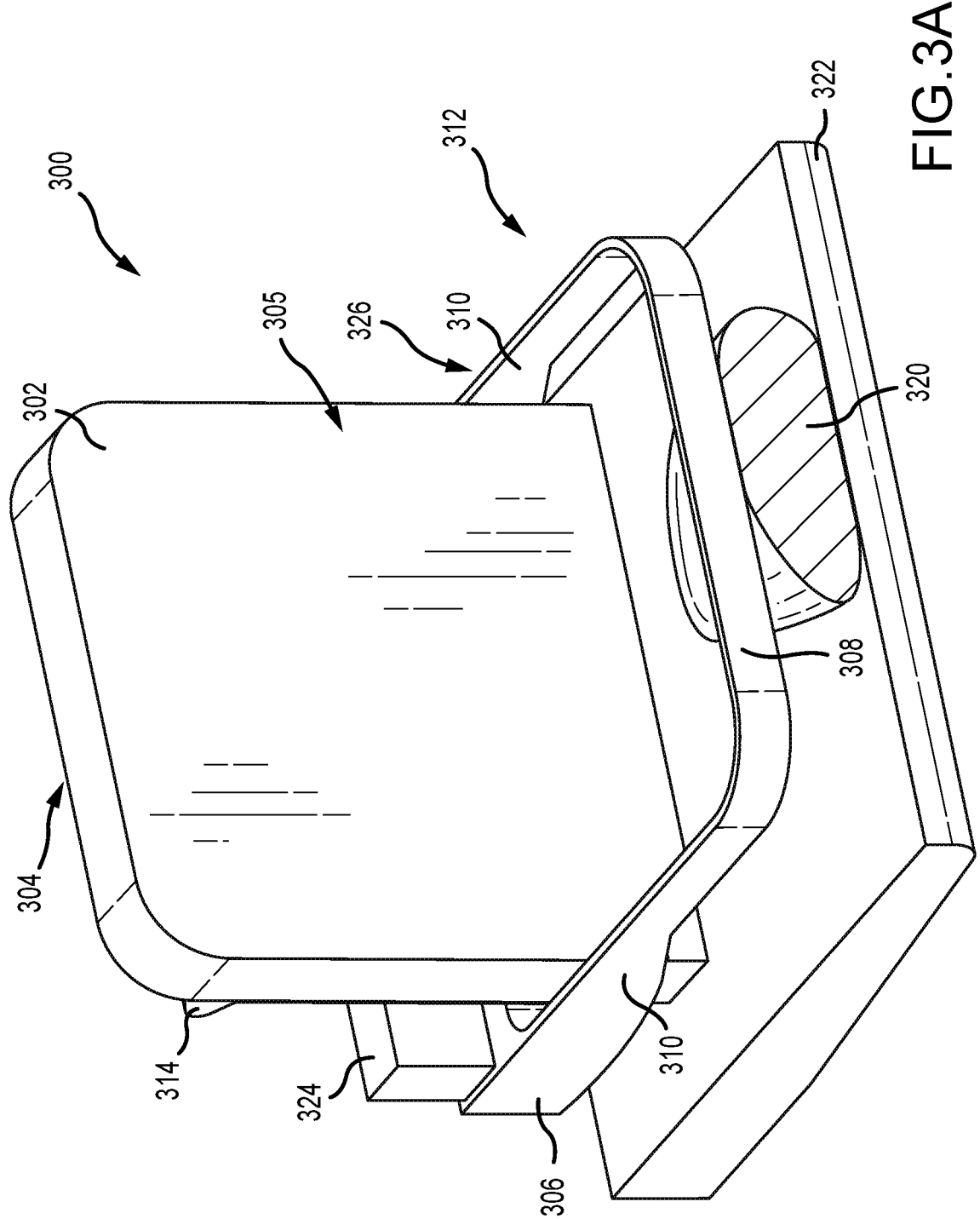
FIGS. 3A-3B depict another example of a compression paddle having a movable foam compressive element, at various positions during compression procedures.
Figure 3B:
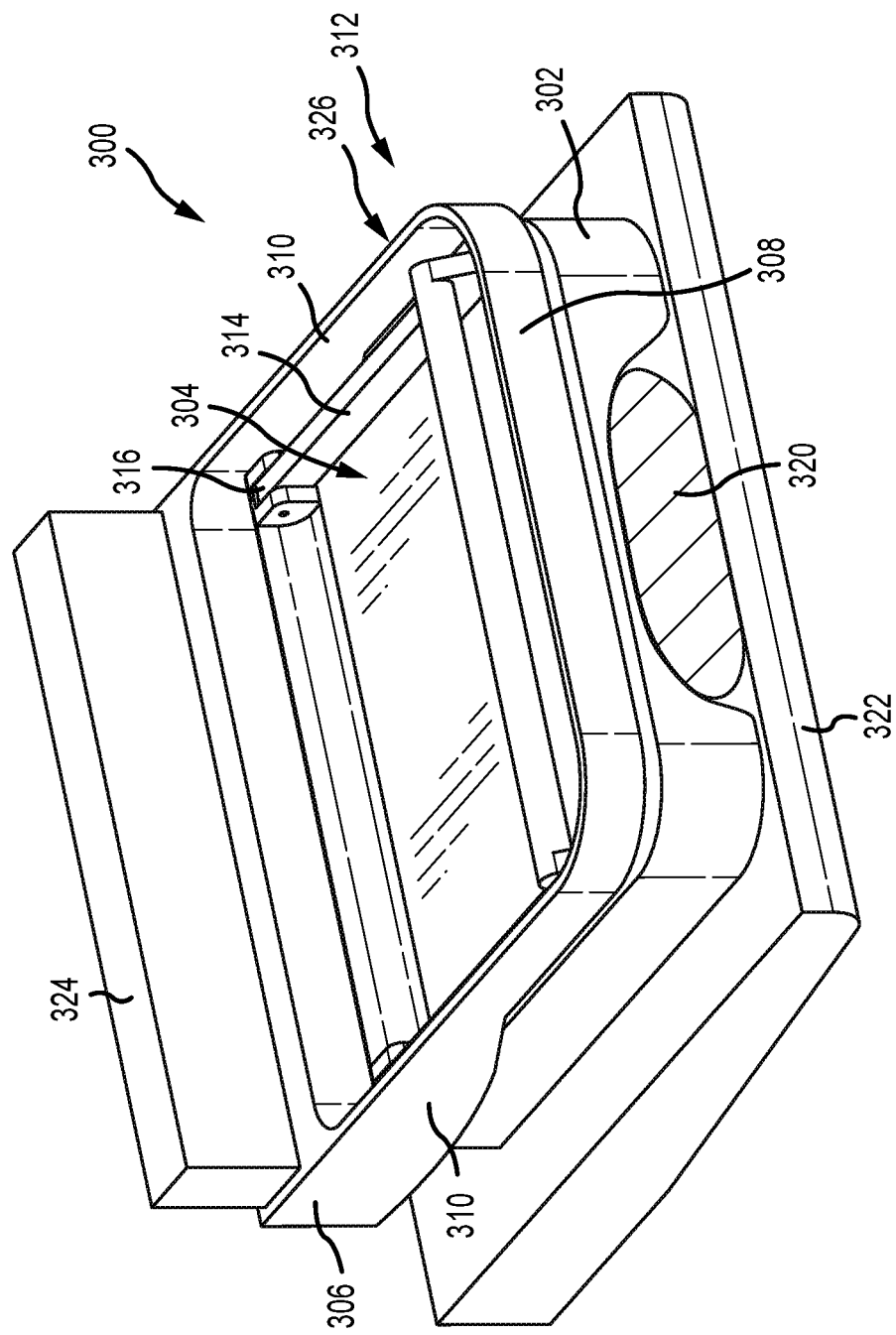

FIGS. 3A and 3B depict another example of a compression paddle 300 having a foam compressive element 302, at various positions during compression procedures. FIGS. 3A and 3B are described concurrently unless noted otherwise. Like the examples above, the compression paddle 300 includes a movable rigid substrate 304 to which the foam compressive element 302 is secured. Unlike the examples above, however, the foam compressive element 302 is only secured to the movable rigid substrate 304 (unlike the examples of FIGS. 2A and 2B where a foam compressive element 202 is secured to the both the underside of the fixed portion of the paddle 200, as well as to the hinged portion 270). Thus, the compression paddle 300 includes a bracket 306, a leading or front wall 308, and a pair of side walls 310 extending from the bracket 306 for removably securing the compression paddle to an imaging system. The leading wall 308 spans the far ends of the side walls 310 so as to form a frame 312 that may be manufactured integral with or discrete from the bracket 306. In this example, the rigid substrate 304 may be formed from the same material as the frame 312. As with other compression paddles depicted herein, the rigid substrate 304 that supports the foam compressive element 302 is pivotably connected to relative to the other portions of the frame 312. The various types of pivotable connections (e.g., living hinges, mechanical hinges, etc. may be utilized). Here, a pivotable strut system 314 is secured to the rigid substrate 304 proximate the bracket 306. In another example, the strut system 314 may be secured directly to the bracket 306, or may be secured to the frame 312 itself (e.g., spanning the two side walls 310). The strut system 314 includes a hinged portion 316 that allows for pivotable movement of the rigid substrate 304 and the attached foam compressive element 302, relative to the frame 312. A cover 305 may substantially surround a bottom portion of the foam compressive element 302, e.g., so as to be taut across a surface thereof.

FIGS. 3A and 3B also depict a breast 320 and a breast support platform 322 upon which the breast 320 rests. The configuration of the compression paddle 300 improves technician visibility of, and access to, the breast 320 during compressive procedures. Since the foam compressive element 302 is entirely opaque, it is advantageous if that component is disposed away from the breast 320 during initial positioning of the breast 320 and lowering of the compression paddle 300 by a compression arm 324. For example, the technician first places the patient breast 320 on the support platform 322. During breast 320 placement, the rigid substrate 304 and attached foam compressive element 302 are in an upward-facing, substantially vertical orientation, as depicted in FIG. 3A. In this position, a significant portion of the foam compressive element 302 is located above a top edge 326 of the frame 312, so the breast 320 remains visible and accessible for the technician. The compression arm 324 lowers the compression paddle 300 until the leading wall 308 substantially contacts the patient's chest wall and, if desired, the top of the breast 320. This helps stabilize the breast 320 for further positioning and subsequent compression. Once the breast 320 is desirably positioned, the technician may pivot the rigid substrate 304 and foam compressive element 302 to the position depicted in FIG. 3B. In this position, the foam compressive element 302 is positioned such that the entire volume thereof is disposed below the upper edge 326 of the frame 312. Further, the strut system 314 may include a locking element to maintain compressive force against the breast 320. Other structures that may be utilized to secure a position of the rigid substrate 304 relative to other components of the compression paddle 300 are described elsewhere herein. The foam compressive element 302 may be pivoted into compressive contact with the breast 320 until a certain desired force is reached. That force may be measured by a strain gauge on the strut system 314, the compression arm 324, or other component. Alternatively, the applied compression force may be determined by other methods known in the art or as described elsewhere herein. Once the foam compressive element 302 is in contact with the breast 320, the compression arm 324 may be further lowered so as to produce a desirable compression force. Thereafter, imaging procedures may be performed, followed by release of the breast 320 from compression.

Figure 4B:
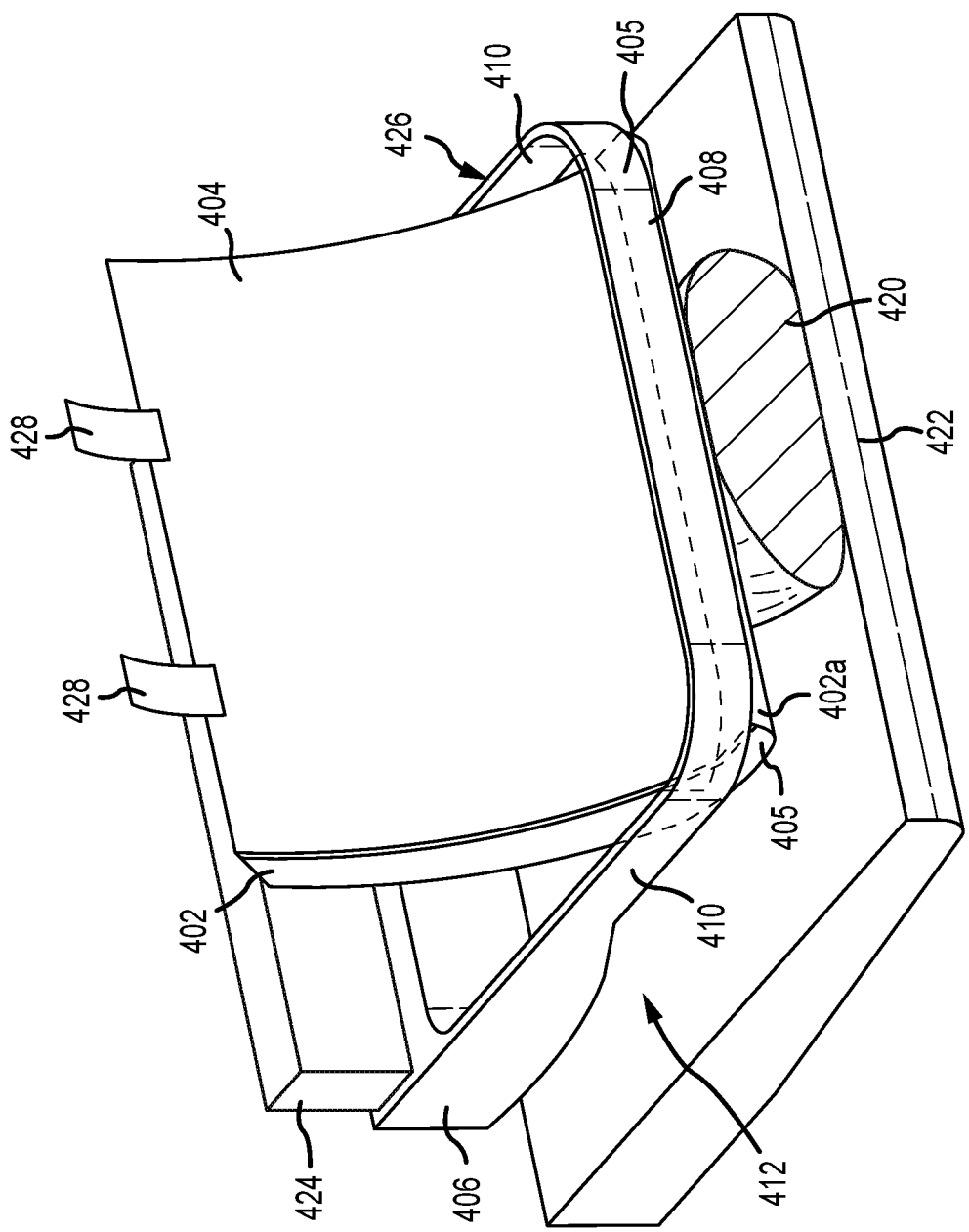
Figure 4C:
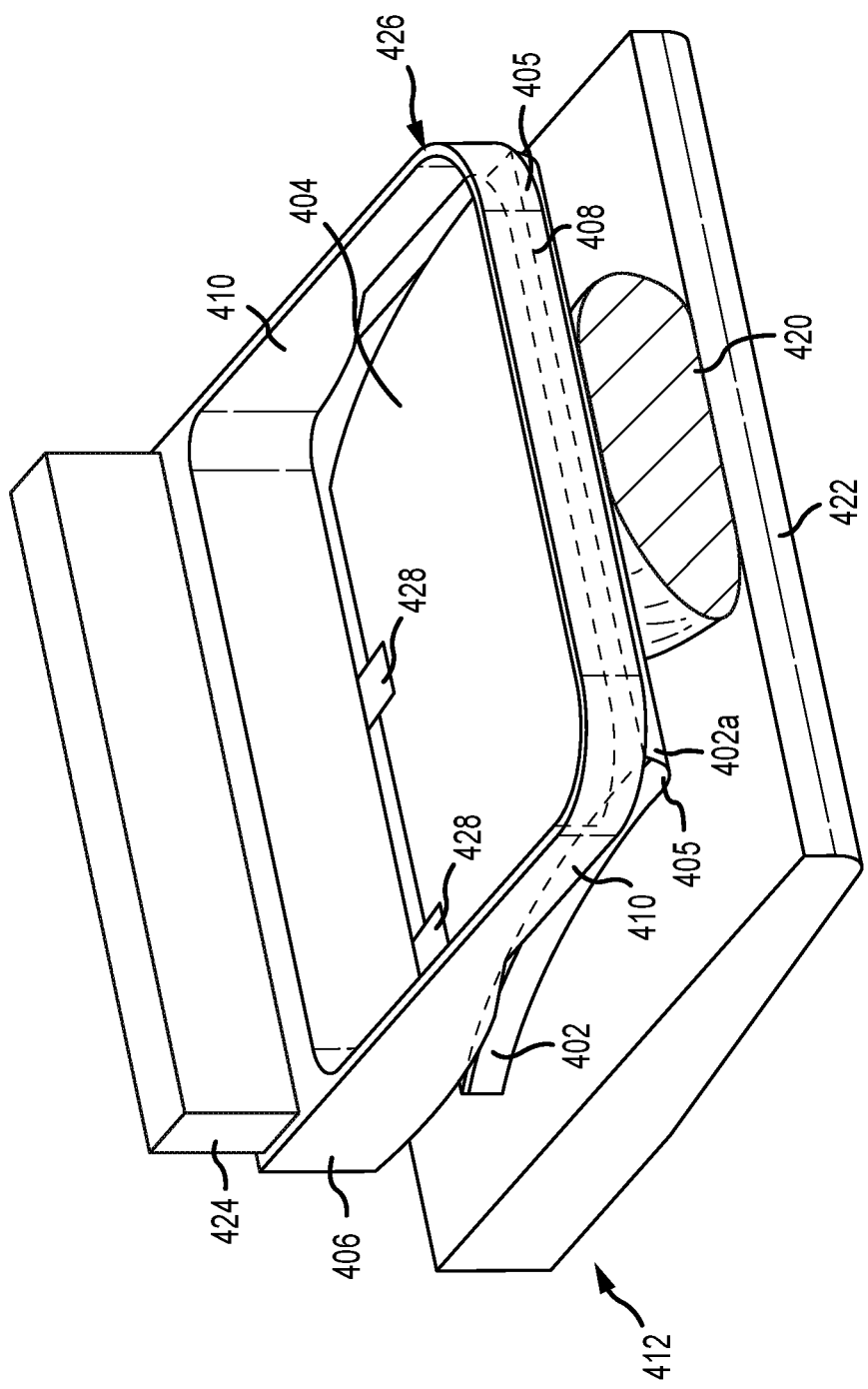

FIGS. 4A-4C depict another example of a compression paddle 400 having a foam compressive element 402, at various positions during compression procedures. FIGS. 4A-4C are described concurrently unless noted otherwise. The compression paddle 400 includes a movable flexible substrate 404 to which the foam compressive element 402 is secured. Use of a flexible substrate 404 (as opposed to a more rigid substrate) may help improve conformance between the compression paddle 400 and a breast 420 during compression thereof. The flexible substrate 404, in this case, is connected to a substantially horizontal bottom portion 405 of a leading wall 408, for example with a living hinge 416. In an example, the flexible substrate 404 may be made of the same material as the other structural portions of the compression paddle 400 (as described below). The compression paddle 400 further includes a bracket 406 and a pair of side walls 410 extending from the bracket 406. The leading wall 408 spans the far ends of the side walls 410 so as to form a frame 412 that may be manufactured integral with or discrete from the bracket 406. In this example, the flexible substrate 404 may be formed from the same material as the frame 412, but made thinner to improve flexibility. In another example, the flexible substrate 404 may be secured to the frame 412 itself (e.g., so as to span the two side walls 410). In another example, a mechanical hinge may be utilized. In another example, the living hinge 416 may be omitted such that only the foam compressive element 402 connects the bottom portion 405 to the flexible substrate 404, such that the foam compressive element 402 acts as the hinge. As with the example of FIGS. 3A-3B, a cover 305 may span the surface of the foam compressive element that contacts the breast 420.

FIGS. 4A-4C also depict a breast 420 and a breast support platform 422 upon which the breast 420 rests. The configuration of the compression paddle 400 improves technician visibility of, and access to, the breast 420 during compressive procedures. For example, the technician first places the patient breast 420 on the support platform 422. During breast 420 placement, the flexible substrate 404 and attached foam compressive element 402 are in an upward-facing, substantially vertical orientation, as depicted in FIG. 4A. In this position, a significant portion of the foam compressive element 402 is located above a top edge 426 of the frame 412, so the breast 420 remains visible and accessible to the technician. A compression arm 424 lowers the compression paddle 400 until the portion of the foam compressive element 402a disposed below the bottom portion 405 substantially contacts a top of the breast 420. Further, the leading wall 408 may contact the patient's chest wall. This helps stabilize the breast 420 for further positioning and subsequent compression and may be more comfortable than contacting the breast 420 with the leading wall 408 alone (e.g., as depicted above in FIGS. 3A and 3B). Once the breast 420 is desirably positioned, the technician may begin to lower the flexible substrate 404 and foam compressive element 402 to an intermediate position depicted for example in FIG. 4B. Further lowering of the flexible substrate 404 and foam compressive element 402 places more of the foam compressive element 402 in contact with the breast 420. In this position, the foam compressive element 402 is positioned such that its entire volume is disposed below the upper edge 426 of the frame 412, for example, as depicted in FIG. 4C. Structures may be utilized to secure a position of the flexible substrate 404 relative to other components of the compression paddle 400. Certain of those structures are described elsewhere herein. In the depicted example, flexible adhesive tabs 428 may be used to fix the position of the flexible substrate 404 relative to the breast platform 422 by adhering the adhesive tabs 426 thereto. Further compressive force may be applied by further lowering of the compression arm 424. Thereafter, imaging procedures may be performed, followed by release of the breast 420 from compression.

Figure 5:
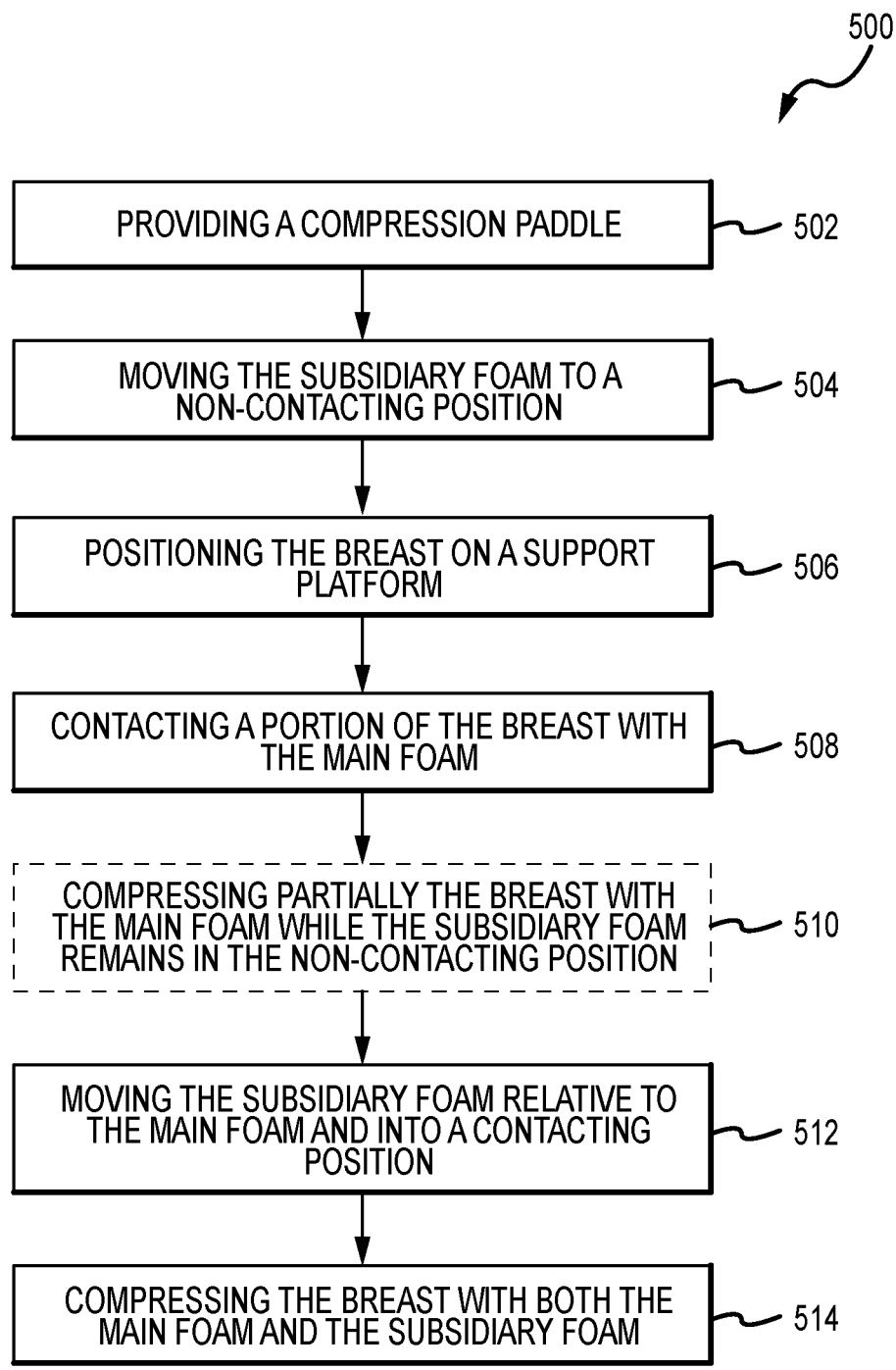
FIG. 5 depicts another method of compressing a breast in an imaging system.

FIG. 5 depicts another method 500 of compressing a breast in an imaging system. The method 500 begins with operation 502, providing a compression paddle. The compression paddle may be as described herein, and may include a main rigid substrate, a main foam secured to the main rigid substrate, and a subsidiary foam movably secured relative to the main foam. Such configurations are depicted and described above, for example, in FIGS. 3A-4B. In operation 504, the subsidiary foam is moved into a non-contacting position. Operation 506 includes positioning the breast on a support platform. Thereafter, operation 508 includes contacting a portion of the breast with the main foam, while the subsidiary foam remains in the non-contacting position. In general, this contact may occur as the compression paddle is lowered towards the breast, either manually or automatically. Optional operation 510 includes at least partially compressing the portion of the breast with the main foam while the subsidiary foam remains in the non-contacting position. Operation 510 is optional because the breast need not be partially compressed. Instead, simply placing the foam in contact with the breast may be sufficient to properly position the breast for further compression. Thereafter, the subsidiary foam is moved relative to the main foam and into a contacting position with the breast, operation 512. Depending on the configuration of the compression paddle, operation 512 may occur in a number of ways. If, for example, a hinged configuration such as that depicted in FIGS. 4A-4B is utilized, moving the subsidiary foam may include pivoting the subsidiary foam and a subsidiary rigid structure connected to the main rigid structure. In another example, moving the subsidiary foam includes positioning the subsidiary foam proximate the main rigid substrate. Moving the subsidiary foam may place the subsidiary foam adjacent the main foam and, in examples, may necessitate securing the subsidiary foam against movement. Once the subsidiary foam is properly positioned, operation 814 includes compressing the breast with both the main foam and the subsidiary foam. Typically compression would increase until the imaging condition is obtained.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A method of compressing a breast for an imaging procedure, the method comprising:
  providing a compression paddle having a main rigid substrate, a main foam secured to the main rigid substrate, and a subsidiary foam movably secured relative to the main foam;

moving the subsidiary foam into a non-contacting position;

positioning the breast on a support platform;

contacting a portion of the breast with the main foam, while the subsidiary foam remains in the non-contacting position;

moving the subsidiary foam relative to the main foam and into a contacting position; and compressing the breast with both the main foam and the subsidiary foam.

2. The method of claim 1, further comprising at least partially compressing the portion of the breast with the main foam while the subsidiary foam remains in the non-contacting position.

3. The method of claim 1, wherein moving the subsidiary foam into the contacting position comprises positioning the subsidiary foam proximate the main rigid substrate.

4. The method of claim 1, wherein moving the subsidiary foam into the contacting position comprises securing the subsidiary foam against movement.

5. The method of claim 1, further comprising locking a position of the subsidiary foam relative to the main foam.

6. The method of claim 1, wherein moving the subsidiary foam comprises pivoting the subsidiary foam.

7. The method of claim 2, wherein moving the subsidiary foam into the contacting position comprises positioning the subsidiary foam adjacent the main foam.

\* \* \* \* \*